(12) United States Patent
Dough

(10) Patent No.: US 9,114,169 B2
(45) Date of Patent: Aug. 25, 2015

(54) SWEETENING AND HEALTHY COMPOSITIONS AND METHODS ASSOCIATED THEREWITH

(71) Applicant: William Gabriel Dough, Greenville, NC (US)

(72) Inventor: William Gabriel Dough, Greenville, NC (US)

(\*) Notice: Subject to any disclaimer, the term of this patent is extended or adjusted under 35 U.S.C. 154(b) by 0 days.

(21) Appl. No.: 14/200,106

(22) Filed: Mar. 7, 2014

(65) Prior Publication Data

US 2014/0255367 A1    Sep. 11, 2014

Related U.S. Application Data

(60) Provisional application No. 61/774,117, filed on Mar. 7, 2013.

(51) Int. Cl.
| | | |
|---|---|---|
| *A23L 1/22* | (2006.01) | |
| *A61K 47/36* | (2006.01) | |
| *A61K 35/742* | (2015.01) | |
| *A61K 31/09* | (2006.01) | |
| *A61K 31/7068* | (2006.01) | |
| *A23L 1/30* | (2006.01) | |
| *A23L 1/221* | (2006.01) | |
| *A23L 2/60* | (2006.01) | |
| *A61K 31/733* | (2006.01) | |
| *A23L 2/52* | (2006.01) | |
| *A23L 1/0528* | (2006.01) | |
| *A23L 1/09* | (2006.01) | |
| *A61K 9/00* | (2006.01) | |

(52) U.S. Cl.
CPC ............... *A61K 47/36* (2013.01); *A23L 1/0528* (2013.01); *A23L 1/09* (2013.01); *A23L 1/221* (2013.01); *A23L 1/30* (2013.01); *A23L 1/3014* (2013.01); *A23L 2/52* (2013.01); *A23L 2/60* (2013.01); *A61K 9/0095* (2013.01); *A61K 31/09* (2013.01); *A61K 31/7068* (2013.01); *A61K 31/733* (2013.01); *A61K 35/742* (2013.01); *A23V 2200/00* (2013.01)

(58) Field of Classification Search
CPC .................................... A23L 1/22; A23L 2/60
See application file for complete search history.

(56) References Cited

U.S. PATENT DOCUMENTS

2011/0229446 A1\*   9/2011   Roman et al. .............. 424/93.45

OTHER PUBLICATIONS

Koplan et. al., Current and Future Public Health Challenges, Journal of the American Medical Association, 284, 1696, (2000).

\* cited by examiner

*Primary Examiner* — Rosanne Kosson
(74) *Attorney, Agent, or Firm* — Ben Schroeder Law, PLLC

(57) ABSTRACT

Formulations are disclosed that contain one or more prebiotics and one or more probiotics. The formulations of the present invention may be used as a supplement that is also a sweetener. The supplement may be useful for anti-aging and/or anti-oxidant properties, increasing mental faculties and/or a decreasing cognitive decline, antibacterial properties, cardiovascular health properties, digestive health benefits such as being effective against irritable bowel syndrome, cognitive health benefits, mental health benefits, anti-inflammatory activity, dry skin treatment, and other benefits.

17 Claims, No Drawings

ID OF THE INVENTION

The present invention relates to sweetening compositions comprising a probiotic and a prebiotic.

BACKGROUND OF THE INVENTION

Americans rapidly increasing consumption of added sugars over the last fifteen years has contributed significantly to a major public health problem, the reversal of which the US Center for Disease Control and Prevention (Koplan and Fleming, J Am Med Assn, 284, 1696, 2000) has targeted as one of its 'top ten' health goals for the 21$^{st}$ century. The problem is the epidemic of obesity in the US. Obesity is defined as a body weight 30% above the ideal body weight. Obesity is strongly linked with greater risk of heart disease, high cholesterol and blood pressure, type 2 diabetes, stroke and breast, colon and prostate cancers. A recent study has shown that more than 50% of Americans are overweight, and 22% are obese.

Probiotics are at times incorporated into dietary supplements because they contain beneficial bacteria or yeast cultures. The Probiotics that comprise beneficial bacteria live in your digestive tract and promote digestive and immune health. Probiotics are intended to bolster the body's naturally occurring intestinal flora and to help natural flora to maintain and/or reestablish themselves. Probiotics are sometimes recommended by doctors and nutritionists to aid in digestion, especially if the natural flora has been destroyed through antibiotic treatments, illness, or other means. However, many types of probiotics don't survive the harsh acidic stomach environment.

Investigation into uses and benefits for probiotics is ongoing, but a number of benefits and therapies have been suggested. For instance, it has been suggested that certain probiotics may be useful in managing lactose intolerance. Lactic acid bacteria, common probiotics, convert lactose into lactic acid; thus their ingestion may help to break down lactose to an extent that allows lactose intolerant individuals to tolerate more lactose than otherwise possible. It has also been suggested that probiotics may be advantageous in prevention of colon cancer, since some probiotics have demonstrated anti-mutagenic effects in the lab setting, apparently due to their ability to bind with heterocyclic amines (carcinogenic substances formed in cooked meat) or by decreasing the activity of certain enzymes that generate carcinogens in the digestive system.

Probiotics may also be useful in lowering cholesterol levels, presumably by breaking down bile in the gut, thus inhibiting its reabsorption (which enters the blood as cholesterol). Probiotics may also lower blood pressure and improve immune function (possibly by means of competitively inhibiting harmful bacterial growth, increasing the number of antibody-producing plasma cells, increasing or improving phagocytosis, and/or increasing the proportion of T lymphocytes and Natural Killer cells).

Foods containing probiotics have also been shown or suggested to have a variety of health effects, including decreasing the incidence of respiratory tract infections and dental caries in children, reducing the incidence of peptic ulcers in adults when used in combination with standard medical treatments, prevention of acute diarrhea, reducing inflammation and hypersensitivity responses, and improving mineral absorption.

Food products and dietary supplements containing viable probiotic cultures have become increasingly popular due to the suggested health benefits associated with such products. The most common forms for probiotics are dairy products and probiotic fortified foods such as yogurt and cheese.

For example, yogurt is a fermented dairy product made by adding lactic acid bacterial cultures to milk, which causes the conversion of sugars (including lactose) and other carbohydrates into lactic acid. It is this process of creating lactic acid that provides the characteristic low pH (about 4.2) and resultant sour taste of yogurt and many other fermented dairy products. To offset the natural sourness of yogurt, it can be sweetened, flavored, or packaged in containers with fruit or fruit jam. Therefore, yogurt manufacturers generally add high amounts of sugar or sugar substitutes to compensate for the sour taste, which makes the product more palatable for many consumers, but results in higher calories. Thus, it would be desirable to be able to decrease calories yet at the same time provide a sweetener that may have added health benefits.

Moreover, the low pH and sourness of yogurt tends to be incompatible with many "ice cream-type" flavors, including for example, vanilla, chocolate, fudge, caramel, marshmallow, nut, coconut, peanut butter, mint, fruit, dulce de leche, butter pecan, cookie dough, and the like as well as combinations thereof. In contrast, a higher pH product (i.e., about 4.8 to about 6.2), which enables better tasting ice cream-type flavors, is associated with a longer shelf life of incorporated probiotic cultures. However, high pH is also associated with an increased and undesirable susceptibility to pathogenic and/or spoilage microbial growth.

Natural cheese has a different anti-microbial system. The growth of undesirable pathogenic and/or spoilage microorganisms is prevented in cheese by a combination of acid developed by the starter cultures, the salt content, and relatively low moisture. The production of other antimicrobial agents by the starter lactic cultures may further boost the antimicrobial properties of the cheese.

Thus, there is a need for supplements/additives/formulations/compositions that have sweetening properties with minimal calories. An added benefit would be present if these supplements/additives/formulations/compositions also contained health benefits.

The present invention provides these and other benefits, as will be apparent from the following description of embodiments of the present invention.

BRIEF SUMMARY OF THE INVENTION

The present invention relates to a synbiotic-sweetener. Synbiotic is an art recognized term that relates to the synergistic benefits of prebiotics (soluble fiber) and probiotics (beneficial gut bacteria). In one embodiment, the present invention relates to a symbiotic-sweetener that also possesses a range of functional health benefits. For example, the synbiotic-sweetener of the present invention may have antioxidant properties, digestive health benefits such as being effective against irritable bowel syndrome, cognitive health benefits, mental health benefits, anti-inflammatory activity, dry skin treatment, and other benefits. In an embodiment the levels of the functional ingredients that are used are within beneficial ranges. In one embodiment, the symbiotic-sweetener has GRAS status (Generally Recognized as Safe status). In an embodiment, the symbiotic-sweetener may also be a food supplement that has medical applications.

DETAILED DESCRIPTION OF THE INVENTION

In an embodiment, the present invention relates to an enhancing sweetener that also has a plurality of health benefits. In an embodiment, the formulations of the present invention are apportioned at exactly the correct size so as to not only provide the perfect amount of sweetener but also to provide optimal health benefits (e.g., the formulations have GRAS status). In an embodiment, the formulations of the present invention are symbiotic sweeteners, which can be ideally added to and/or taken with hot beverages and breakfast food items such as coffee, tea, oatmeal, breads, yogurt, cheeses, smoothies, juices, etc. In an embodiment, the formulations of the present invention may be organic; vegan; kosher; have a low glycemic index; and be an excellent source of fiber.

In an embodiment, the composition of the present invention serves as sweetener and can be added to any one or more member from the following list of edible foodstuffs to generate a sweetened edible formulation. The subject sweetener is useful for sweetening a large number of edible foodstuffs, including processed beverages such as carbonated and non-carbonated soft drinks, fruit drinks, flavored dairy drinks, vegetable juices, egg nogs, wines, liqueurs, coffee, or tea; including processed foods such as sweet baked goods, breads, dairy desserts, breakfast cereals, hard candies, meats processed with sweet liquors, custards, salad dressings, vegetable pastes and sauces, condiments such as catsup and salsa, pickles and relishes, ice creams, sherbets and flavored ices, ice milk products, icings, confections and confection toppings, syrups and flavors, jams and jellies, cake and pastry mixes, and pie fillings; including functional/nutritional foods such as sports drinks, nutrition bars, nutrition powders and gels, probiotic yogurt and cultured dairy foods, and nutritional supplements; and is useful as a tabletop sweetener. Other edible formulations that may be sweetened by the subject sweetener include pharmaceutical and nutraceutical products requiring a sweetener/excipient and pet foods.

In an embodiment, the compositions and methods of the present invention allow the composition to be sold as additives that can be added to products that are available at coffee and bagel shops, cafes, grocery, health clubs, and/or convenience stores.

In an embodiment, the present invention has a delightful and unique flavor/aroma and may be added to breakfast foods.

In an embodiment, the present invention has perfect portion size. The portion controlled packages may be served so that they are limited to a serving size that comprises a healthy amount. In one embodiment, the serving size is between about 5 and 50 ml or between about 5 and 30 ml or between about 5 and 25 ml or between about 10 and 20 ml or between about 10 and 15 ml or about 10 ml. The composition of the present invention (which is the perfect serving size) may be taken by itself, or alternatively, it may be added to foods that need sweetening.

In an embodiment, the present invention is about 95% organic or alternatively, about 90% organic, or about 80 organic. In an embodiment, the composition of the present invention is suitable for vegans; and/or alternatively and/or additionally it may be kosher; and/or alternatively and/or additionally it may have a Low glycemic index; and/or alternatively and/or additionally it may be an excellent source of fiber.

In embodiments of the present invention, the composition may be used to treat any of a number or maladies. For example, the functional aspects of the invention may act as an antioxidant, or treat digestive maladies and/or alternatively, treat cognitive disorders and or alternatively and/or additionally treat cardiovascular systems and diseases. The formulations of the instant invention can also be used to treat eczema.

In an embodiment, the present invention relates to a composition comprising Agave Inulin, which has a plurality of functionalities including serving as a good source of fiber. In one embodiment, the compositions of the present invention contain Agave Inulin in an amount that contains about 5 g of fiber per serving. The composition of the present invention, which contains Agave Inulin, also lowers LDL and LDL cholesterol, thus, being good for those that have cardiovascular issues. The composition of the present invention, which contains Agave Inulin also, is useful at improving the immune health of individuals that consume the composition. The composition of the present invention, which contains Agave Inulin, also serves as a prebiotic, which optimizes the conditions for any composition that also contains probiotics. The composition of the present invention, which contains Agave Inulin, also can be used in a composition that serves as a sweetener, wherein said composition is devoid or largely devoid of calories. Thus, when the composition serves as a sweetener, the composition can be used in methods of losing weight.

In an embodiment, the composition of the present invention contains Agave Inulin and Pterostilbene (Pteropure). The composition of the present invention, which in an embodiment, contains Agave Inulin and Pterostilbene in addition to being used for the immune health of individuals, for reducing LDL and LDL cholesterol levels, and as a good source of fiber also can be used for anti-aging due to its anti-oxidant activity, for anti-anxiety, for cognitive enhancement and for cardiovascular health. Without being bound by the mechanism of action, pterostilbene is similar in structure and also in functionality to resveratrol (they differ in that pterostilbene has a 3,5-dimethoxy benzene functionality whereas resveratrol has alcohol functionalities instead of methoxy groups—both of which, are phytoalexins) which is the anti-oxidant found in blueberries. Pterostilbene, thus, has the beneficial anti-oxidant effects of blueberries but has three to four times better bioavailability relative to resveratrol. The half-life of pterostilbene in the human body is seven times longer than resveratrol. Pterostilbene also has greater absorption and metabolic stability and 2-4 times greater cellular uptake relative to resveratrol.

Pterostilbene promotes heart health by helping to maintain healthy systolic and diastolic blood pressure levels already within normal ranges. It supports healthy blood flow and circulation. It likely improves memory and mental focus. It may enhance mood and a feeling of well-being while simultaneously providing a calming influence including reducing stress, anxiety, and nervous tension. It is also thought to support healthy blood sugar levels by raising the body's production of insulin. It supports healthy metabolism and helps regulate the body's use of energy and is thought to be useful for weight loss.

In one embodiment, the amount of pterostilbene present in the composition is an amount equivalent to 2000 pounds of blueberries to get the same beneficial effects. In an alternate embodiment, the amount of pterostilbene present in the composition is an amount equivalent to 2100 pounds of blueberries to get the same beneficial effects. In an alternate embodiment, the amount of pterostilbene present in the composition is an amount equivalent to 2150 pounds of blueberries to get the same beneficial effects. In an alternate embodiment, the amount of pterostilbene present in the composition is an amount equivalent to 2200 pounds of blueberries to get the same beneficial effects.

Pterostilbene may also have anti-aging and/or antioxidant effects by fighting the presence of free radicals caused by oxidative stress. Pterostilbene supports healthy cellular aging with powerful anti-oxidant activities. Pterostilbene is thought to promote nitric oxide synthesis via the ENOS pathway (Endothelial Nitric Oxide Synthase pathway), which means it may advance healthy recovery and it may improve mitochondrial function.

In an embodiment, the present formulation may comprise a composition that contains one or more stilbenes sufficient to have desired antioxidant effects. Alternatively, in an embodiment, the one or more stilbenes present may have a beneficial anti-inflammatory effects. In an alternate embodiment, the present invention may contain one or more stilbenes that are efficacious in reversing cognitive behavioral deficits. In an embodiment, the formulations of the present invention may be effective against Alzheimer's. In an alternate embodiment, the present invention may contain one or more stilbenes that are efficacious in releasing dopamines and/or helping the memory.

Stilbenes that may be used in the present invention include one or more of resveratrol, pinostilbene, desoxythapontigenin, pterostilbene, pterostilbene glucoside, 3-hydroxy pterostilbene, resveratrol trimethylether, and/or piceatannol.

In an embodiment, a probiotic is added to the composition of the present invention. In an embodiment, the probiotic is *Bacillus coagulans* GBI-30 (BC30), BC30 is an ideal probiotic for the present invention because it is able to survive the acidity of the stomach so it can reach the intestines where it undergoes its mode of action. BC30 contains a natural protective layer of proteins, which allows it to not only survive the harsh environment of the stomach, but allows it to survive most manufacturing processes. Moreover, it provides it with stability at elevated temperatures, it provides it with an extended shelf life relative to other probotics, is able to survive exposure to bile, and it has also achieved GRAS status. The fact that BC30 is resistant to elevated temperatures means that it can be used in hot foods and/or beverages and still provide the health benefits alluded to herein.

The fact that BC30 has the stability traits alluded to above allows it to have a greater deliver of helpful bacteria to the part of the digestive tract where it is needed (e.g., in the intestines). It has been found that BC30 may return to levels seen prior to supplementation after taking the supplements ceases. Moreover, other bacteria and/or probiotics in the gut generally return to levels seen prior to supplementation after one ceases taking a BC30 supplement.

BC30 may also be beneficial to those individuals that are taking antibiotics. Often, when one takes antibiotics, the bacteria in the intestines are killed. Because BC30 are bacteria, they may replace these bacteria. Accordingly, in an embodiment, the present composition may be taken in conjunction with an antibiotic. For example, the formulations of the present invention may include the penicillins, amoxicillin, amoxicillin-clavulanate (Augmentin), the cephalosporins such as cephalexin, celadroxil, cephradinc, cefaclor (Ceclor), cefuroxime (Ceftin), cefprozil (Cefzil), loracarbef (Lorabid), cefpodoxime (Vantin), cefdinir (Omnicef) cefditoren (Sprectracef), cefixime (Suprax), ceftibuten (Codex) or Ceftriaxone (Rocephin). Other anti-bacterials that may be present in the formulation of the present invention include Macrolides, Trimethoprim-Sulfamethoxazole, Fluoroquinolones (Quinolones) such as levofloxacin (Levaquin), gatifloxacin (Tequin), and moxifloxacin (Avelox), Lincosamides and tetracyclines such as doxycycline, tetracycline, and minocycline.

Moreover, BC30 may also out-compete other harmful bacteria that cause infections or may have some other deleterious effect. BC30 may delay the onset of symptoms and a quicker recover from infection and/or colitis caused by *Clostridium dificile*. *Clostridium dificile* is known to sicken more than half a million people a year causing 15 to 20 thousand deaths annually. Other methods that are used to treat infections caused by *Clostridium dificile* cost more than 3 billion dollars per year and result in over 2 million days of hospitalization time.

Thus, the formulations of the present invention may also comprise and/or be taken in conjunction with an antibiotic, an antifungal, anti-inflammatory agent or an antiviral agent, or any combination thereof.

Antifungal agents for use herein include any agent effective in reducing the possibility of fungus being present. Examples of antifungal agents that can be used with the formulations of the present invention include oral steroids such as Triamcinolone (Nasacort) Mometasone furoate (Nasonex), Fluticasone (Flonase, Flounce), Beclomethasone (Beconase, Vancenase), flunisolide (Nasalide), and budesonide (Rhinocort). Other anti fungal agents that can be used include flumetasone, ketoconazole, amphotericin B, itraconazole, nystatin, fluconazole and/or clioquinol.

In an embodiment of the present invention, the formulation has a delightful unique flavor and aroma that's perfect for breakfast foods such as coffee, tea, toast, bagels, oatmeal, yogurt, smoothies and the like. In one embodiment, it comes in a portion controlled packet so that it not only has limited calories, but it also has maximal health benefits. The formulations of the present invention may come in individual serving sizes and can be simply added to the food to which it is to be added. Alternatively, the single serving size may be taken independent of other food. The formulations/supplements/packets/individual serving size of the present invention may be of a size that is suitable to be taken by any one. In an embodiment, the formulations may be taken by baby boomers, wherein the formulation is used primarily for both long and short-term health benefits/anti-aging effects. Baby boomers are known to undergo supplement fatigue, wherein baby boomers may have trouble chewing and swallowing pills (e.g., supplements). Accordingly, in an embodiment, the present invention relates to having a formulation that is in a liquid form that prevents the baby boomers from having to chew supplements. The liquid can either be taken alone or may be added to either a liquid or a solid drink or food. Alternatively and/or additionally the formulation of the present invention may be a powder form that is dissolvable in liquids or can be mixed in with food so that supplement pills do not have to be chewed by baby boomers (or by others). If the formulation is in powder form it can be simply sprinkled on top of foods and ingested in that manner (e.g., like salt and pepper or other spices).

Alternatively and/or additionally, the formulations of the present invention are suitable for professionals and/or college students wherein the formulation is primarily used for focus and/or for short-term cognitive benefits. Alternatively and/or additionally, the formulations of the present invention are suitable for endurance athletics wherein the formulation is used primarily for the attributes associated with sugar and pterostilbene. Alternatively and/or additionally, the formulations of the present invention are suitable for those people that are trying to avoid supplemental fatigue. In this regard, the formulations of the present invention may additionally have a stimulant in it such as caffeine.

In an embodiment, other probiotic cultures may be used in combination with the composition of the present invention. Suitable probiotic cultures for use with the present invention may be readily selected by one of ordinary skill in the art and may include, for example, various species of the genera *Bifidobacterium, Lactobacillus*, and *propionibacteria* such as: *Bifidobacterium animalis* subsp. *lactis; Bifidobocterium bifidum; Bifidobacterium breve; Bifidobacterium infantis; Bifidobacterium longum; Lactobacillus acidophilus; Lactobacillus casei; Lactobacillus plantarum; Lactobacillus reuteri; Lactobacillus rhamnosus; Lactobacillus spoogenes* and the like. A species of yeast *Saccharomyces boulardii*, may also be used as a probiotic. In an embodiment, the probiotic cultures include *Bifidobacterium lactis* BI-04, *Bafidobacterium lactis* BB-12 (CHN), and *L. reuteri* (SD 55730—Biogaia).

The probiotic cultures are preferably present in an amount of approximately $1 \times 10^9$ cfu/per serving. In one form, a serving size is at least about 2 g, preferably at about 5 g to about 25 g. As will be readily apparent to one of ordinary skill in the art, the amount of probiotic cultures to be incorporated depends on a number of factors including, for example, serving size, type of probiotic culture, and the expected loss rate over shelf life. Thus, in one preferred form, probiotic cultures are incorporated in the dairy composition at a level of about 1.times.10.sup.4 cfu/g to about 1.times.10.sup.9 cfu/g.

The dairy composition may optionally include one or more additional components including, for example, but not limited to, flavor(s), fat(s), protein(s), other prebiotic(s) sweetener(s), thickener(s), pH adjuster(s), colorant(s), vitamin(s), mineral(s) calcium, bulking agent(s), spices, collagen, characterizing ingredient(s), such as cocoa, salt, fruit pieces, puree, or juice, botanical extracts, and/or combinations thereof.

The flavor component may be added in any suitable amount and may include any suitable flavor and/or aroma source. In one form, the flavor component is an ice cream-type flavor, such as vanilla, chocolate, fudge, caramel, marshmallow, nut, coconut, peanut butter, mint, fruit, dulce de leche, butter pecan, cookie dough, and the like, as well as combinations thereof. Other flavors that can be used include cinnamon (both Chinese and Ceylon), allspice berries spice, nutmeg, lemon, lime, pistachio, or cloves.

Thus, in one embodiment, the present invention advantageously provides a new way to enjoy a dairy product with cultures, which enables a more appealing flavor profile than conventional fermented dairy products and satisfies appropriate microbial food product safety precautions. Because the composition of the present invention in an embodiment also acts as a sweetener, it is possible to preclude the use of sugar or other sweetener, thus reducing the caloric value.

Fat components suitable for use with the present invention may include any suitable fat source containing any edible natural, synthetic, or modified solid fat, liquid oil, fat substitute, obtained from any suitable plant, animal, or other source. In a preferred form, the fat component is milkfat. Preferably, fat is present in the dairy composition in an amount of less than about 20%, or less than about 10%, or less than about 5%, by weight of the dairy composition.

The protein component may include any suitable protein source, including, for example. whey protein (e.g. whey protein concentrate or isolate) milk protein (e.g. non-fat dry milk, milk protein concentrate or isolate), soy protein (e.g. soy protein concentrate or isolate), UF milk, concentrated milk, and/or combinations thereof. Preferably, the protein is present in the dairy composition in an amount of at least about 3%, and, in some cases, as much as 10% or more by weight of the dairy composition.

Suitable prebiotic components for use with the present invention may include, for example, inulin and oligosaccharides such as manno-oligosaccharides, galacto-oligosaccharides, and fructo-oligosaccharides. The prebiotic component may be incorporated in any suitable amount, generally up to about 3%, and, in some cases, up to about 10%, by weight of the dairy composition.

Other sweeteners might also be added to the composition of the present invention. For example, sweetener components suitable for use with the invention include, for example, natural sweeteners such as sucrose, glucose, fructose, maltose, lactose, galactose, high fructose corn-syrup, artificial intensive sweeteners, and sugar alcohols. Natural sweeteners may be incorporated in any suitable amount, generally up to about 20%, by weight of the dairy composition. Artificial intensive sweeteners and/or sugar alcohols may be incorporated in any suitable amount, generally from about 0.001% to about 20% or from about 0.001% to about 5%, or from about 0.05% to about 2%.

Suitable thickening components may include, for example, starches and gums. The thickening component may be incorporated in any suitable amount (for a starch, generally about 1.0% to about 2.5% and for a gum, generally about 0.1% to about 0.5%, by weight of the composition).

Preferably a pH adjusting component, such as lactic acid, citric acid, fumaric acid, hydrochloric acid, sodium acid sulfate and calcium acid sulfate is incorporated in an amount sufficient to adjust the pH of the dairy composition to a desirable pH, preferably about 4.8 to about 6.2, and more preferably about 5.0 to about 6.0. Alternatively, all or part of the dairy composition may be cultured to the appropriate pH. In the case of a cheese-type product, the addition of rennet may be utilized.

In one embodiment, the formulation of the present invention is produced under sterile conditions. In addition to or in lieu of sterilization, the formulations of the present invention may contain a pharmaceutically acceptable preservative to extend shelf life. Additionally, a pharmaceutically-acceptable preservative may be used in the present formulations to increase the stability of the formulations. It should be noted, however, that any preservative must be chosen for safety. Preserving agents may also be present in an amount from about 0.001% to about 1%, or alternatively, from about 0.002% to about 0.02% by total weight or volume of the formulation.

The present formulations may further comprise from about 0.01% to about 90%, or about 0.01% to about 50%, or about 0.01% to about 25%, or about 0.01% to about 10%, or about 0.01% to about 1% w/w of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration in some embodiments is determined by the e presence or absence of the other ingredients in the formulation. The excipients and additives may include, but are not limited to, surfactants, moisturizers, stabilizers, complexing agents, antioxidants, solubilizing agents, emulsifying agents, suspending agents, sweetening agents or other additives known in the art.

The formulation of the present invention may additionally contain pharmaceutically acceptable salts, solvates, and prodrugs thereof, and may contain antiseptics, astringents, diluents, excipients, carriers, micelles, liposomes, or other substances necessary to increase the bioavailability or extend the lifetime of the compounds/bacteria present in the composition of the present invention. The present invention is not only directed to compositions but is also directed to formulations, supplements, sweeteners, medicaments, and other products and methods of using those products, formulations, supplements, sweeteners, and medicaments.

EXAMPLES

Example 1

65% by weight of organic agave syrup and 35% by weight organic agave inulin were combined to give the base formula. The base formula was mixed with high shear from the bottom up so as to avoid aeration of the mixture. The agave inulin was blended from underneath the agave syrup. The agave inulin acts as emulsifier in the resulting mix.

To this mix was added flavoring comprising 6 grams of Cinnamon was added flat every 1 kg of base formula to give the flavored formula.

To the flavored formula were added 20 mg, pterostilbene (Pteropure) per every 10 ml of flavored formula and 67 mg Probiotic (BC 30) per every 10 ml of flavored formula to give the Agave Shot formula. It is noted that the density of the flavored formula is 1.44 g/ml. In the example, pteropure is not placed in direct contact with BC30 in order to maintain the strict integrity of the ingredients. BC30 is the last ingredient added. During the mixing procedure, all of the ingredients are protected from light, air and moisture.

Example 2

In a scaled up procedure, one example contained 650 kg agave syrup, 350 kg agave inulin, 8 kg cinnamon, 1.143 kg pteropure and 4.786 kg. BC30.

Example 3

In Example 3, the composition is made the same way as in example 1 except functional ingredient citicoline is also added. In one embodiment of Agave Shot 50 mg to 250 mg of citicoline is added in addition to the current functional ingredients per 10 ml of flavored formula. As an alternative to cinnamon, the formula will include flavors such as chocolate, vanilla, or the like.

In an embodiment the present invention relates to a composition comprising at least one of pterostilbene and BC 30, and at least one of agave inulin and agave syrup. In a variation, the composition comprises both pterostilbene and BC 30. In a variation, the composition comprises pterostilbene, BC 30, agave inulin, and agave syrup. In a variation, the composition further comprises a flavoring. In an embodiment, the flavoring is cinnamon.

In an embodiment, the present invention relates to a composition comprising at least one member selected from each of group I, group II and group III wherein group I comprises one or more members selected from the group consisting of Bacillus coagulans GBI-30, Bifidobacterium animalis lactis, Bifidobacterium bifidum, Bifidobacterium breve, Bifidobacterium infantis, Bifidobacterium longum, Lactobacillus acidophilus, Lactobacillus casei, Lactobacillus plantarum, Lactobacillus reuteri, Lactobacillus rhammosus, and Lactobacillus spoogenes, group II comprises one or more members selected from the group consisting of resveratrol, pinostilbene, desosythapontimnin, pterostilbene, citicoline, pterostilbene glucoside, 3-hydroxy pterostilbene, resveratrol trimethylether, and piceatannol; and group III comprises one or more members selected from the group consisting of agave inulin and agave syrup.

In an embodiment, the composition further comprises at least one of fats, proteins, other prebiotic sweeteners, thickeners, pH adjusters, colorants, vitamins, minerals calcium, bulking agents, spices, and characterizing ingredients.

In an embodiment, the composition may contain citicoline instead of pterostilbene. Alternatively, the composition may further comprise citicoline.

In an embodiment, the present invention relates to a sweetener. In an embodiment, the sweetener comprises at least one of pterostilbene and BC 30, and at least one of agave inulin and agave syrup. In a variation, the sweetener comprises both pterostilbene and BC 30. In a variation, the sweetener comprises pterostilbene, BC 30, agave inulin, and agave syrup.

In an embodiment, the sweetener may have one or more of fats, proteins, other prebiotic sweeteners, thickeners, pH adjusters, colorants, vitamins, minerals calcium, bulking agents, spices, and characterizing ingredients. In an embodiment, the sweetener may comprise citicoline either in addition to pterostilbene or in place of pterostilbene.

In an embodiment, the sweetener comes packaged in individual serving sizes. In an embodiment, the individual serving size is between about 5 ml and about 20 ml or alternatively between about 10 ml and about 15 ml or between about 10 ml and 12 ml or alternatively about 10 ml.

In an embodiment, the present invention relates to a method of sweetening food or drink comprising adding a formulation to said food or drink wherein the formulation comprises pterostilbene, BC 30, agave inulin, and agave syrup. In a variation, the composition of the method comprises a flavoring. In an embodiment, the method uses a composition that may comprise citicoline either in addition to pterostilbene or in place of pterostilbene.

In an embodiment, the present invention relates to a method of increasing mental faculties and/or reducing cognitive decline of an individual comprising administering to said individual a composition comprising one or more of pterostilbene and citicoline, one or more of agave inulin and agave syrup, and BC30. In one embodiment, pterostilbene and citicoline are present in the composition together. Without being bound by a mechanism of action, it is believed that pterostilbene and citicoline act by different mechanisms of action and thus, the effects of pterostilbene and citicoline may prove to be synergistic rather than simply additive in effect.

Moreover, the combination of pterostilbene with prebiotics and probiotics may in fact be synergistic.

In one embodiment, the prebiotics come from agave. In an embodiment, the prebiotics may be in the form of agave inulin or agave syrup or alternatively, both. In certain embodiments, the prebiotics (which is an indigestible polysaccharide) comes from vegetables. Examples of vegetables from which the prebiotic may be isolated include artichokes, garlic, leeks, onions and chicory. In an embodiment, the prebiotics may come from soy beans and products made from soybeans such as tofu. Inulin may be present in any concentration and be present in any of a number of forms (e.g., it polymeric that when it undergoes hydrolysis yields mainly fructose) and be derived from any of the food groups enumerated herein.

In an embodiment, the methods of the present invention allow the composition to be added to food or drink, which may be one or more members selected from the group consisting of carbonated soft drinks, non-carbonated soft drinks, fruit drinks, flavored dairy drinks, vegetable juices, egg nogs, wines, liqueurs, coffee, tea; baked goods, dairy desserts, breakfast cereals, hard candies, meats, custards, salad dressings, vegetable pastes, vegetable sauces, catsup, salsa, pickles, relishes, ice creams, sherbets, flavored ices, ice milk products, icings, confections, confection toppings, syrups, flavors, jams, jellies, cake, pastry mixes, pie fillings; pizza dough, sports drinks, nutrition bars, nutrition powders, nutrition gels, probiotic yogurt and cultured dairy foods. In an embodiment, the methods of the present invention may use a composition that further comprises one or more of flavoring agents, fats, proteins, other prebiotics, thickeners, pH adjusters, colorants, vitamins, minerals calcium, bulking agents spices, or characterizing ingredients.

It is contemplated and therefore within the scope of the invention to include reasonable modifications to the embodiments described above without departing from the spirit and scope of the invention. For example, it is contemplated and therefore within the scope of the invention that any one or more feature(s) that is/are described herein can be combined with any other one or more feature(s) irrespective of the fact that those features may not be mentioned with the same product. It should be understood that when a range is given, any and all numbers that fit within the scope of the range are contemplated as potential and points. Moreover, it is contemplated and therefore within the scope of the invention when Markush groups are given that any subset of those substituents can be used to generate a Markush sub-group. In any event, the present invention is to be described by the below claims.

I claim:

1. A composition comprising pterostilbene, *Bacillus coagulans*, strain BC 30, and agave inulin.

2. The composition of claim 1, wherein the composition comprises pterostilbene, BC 30, agave inulin, and agave syrup.

3. The composition of claim 2, wherein the composition further comprises a flavoring.

4. The composition of claim 3, wherein the flavoring is cinnamon.

5. The composition of claim 2, further comprising at least one of fats, proteins, other prebiotic sweeteners, thickeners, pH adjusters, colorants, vitamins, minerals, calcium, bulking agents, spices, and characterizing ingredients, wherein the characterizing ingredients are selected from the group consisting of cocoa, salt, fruit pieces, fruit puree, fruit juice and botanical extracts.

6. The composition of claim 2, wherein the composition further comprises citicoline.

7. A sweetener comprising pterostilbene, *Bacillus coagulans*, strain BC 30, and agave inulin.

8. The sweetener of claim 7, wherein the composition comprises pterostilene, BC 30, agave inulin, and agave syrup.

9. The sweetener of claim 8, further comprising at least one of fats, proteins, other prebiotic sweeteners, thickeners, pH adjusters, colorants, vitamins, minerals, calcium, bulking agents, spices, and characterizing ingredients, wherein the characterizing ingredients are selected from the group consisting of cocoa, salt, fruit pieces, fruit puree, fruit juice and botanical extracts.

10. The sweetener of claim 8, further comprising citicoline.

11. The sweetener of claim 8, wherein the sweetener comes packaged in individual serving sizes.

12. The sweetener of claim 11, wherein the individual serving size is between about 5 ml and about 20 ml.

13. The sweetener of claim 12, wherein the individual serving size is between about 10 ml and about 15 ml.

14. A method of sweetening food or drink comprising adding a formulation to said fund or drink wherein the formulation comprises pterostilbene, BC 30, agave inulin, and agave syrup.

15. The method of claim 13, wherein the formulation further comprises a flavoring.

16. The method of claim 14, wherein the formulation further comprises citicoline.

17. The method of claim 14, wherein the food or drink is one or more members selected from the group consisting of carbonated soft drinks, non-carbonated soft drinks, fruit drinks, flavored dairy drinks, vegetable juices, egg nogs, wines, liqueurs, coffee, tea; baked goods, dairy desserts, breakfast cereals, hard candies, meats, custards, salad dressings, vegetable pastes, vegetable sauces, catsup, salsa, pickles, relishes, ice creams, sherbets, flavored ices, ice milk products, icings, confections, confection toppings, syrups, flavors, jams, jellies, cake, pastry mixes, pie fillings; sports drinks, nutrition bars, nutrition powders, nutrition gels, probiotic yogurt and cultured dairy foods.

* * * * *